United States Patent
Hegazi et al.

(10) Patent No.: US 10,060,899 B2
(45) Date of Patent: Aug. 28, 2018

(54) CHARACTERIZING LUBRICANT OIL DEGRADATION USING FLUORESCENCE SIGNALS

(71) Applicant: Saudi Arabian Oil Company, Dhahran (SA)

(72) Inventors: Ezzat Hegazi, Ontario (CA); Vincent Cunningham, Ferbane (IE); Maha Nour, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/496,953

(22) Filed: Apr. 25, 2017

(65) Prior Publication Data

US 2017/0307584 A1 Oct. 26, 2017

Related U.S. Application Data

(60) Provisional application No. 62/327,558, filed on Apr. 26, 2016.

(51) Int. Cl.
*G01T 1/167* (2006.01)
*G01N 33/28* (2006.01)
(Continued)

(52) U.S. Cl.
CPC ........ *G01N 33/2888* (2013.01); *G01J 3/4406* (2013.01); *G01J 3/46* (2013.01);
(Continued)

(58) Field of Classification Search
CPC ............... G01N 33/2888; G01N 21/94; G01N 33/2858; G01N 33/30; G01N 2201/062;
(Continued)

(56) References Cited

U.S. PATENT DOCUMENTS 4,031,398 A 6/1977 Callis et al.
4,651,010 A 3/1987 Javan
(Continued)

FOREIGN PATENT DOCUMENTS

FR 2817346 A1 5/2002

OTHER PUBLICATIONS

Van-Den-Begin et al., "Fast adsorption-desorption kinetics of hydrocarbons in silicalite-1 by the single-step frequency response method," Zeolites, vol. 9, No. 4, Jul. 1989; pp. 287-292, <http://dx.doi.org/10.1016/0144-2449(89)90073-0>.

(Continued)

*Primary Examiner* — Taeho Jo
(74) *Attorney, Agent, or Firm* — Fish & Richardson P.C.

(57) ABSTRACT

Methods, systems, and apparatus to diagnose lubrication oil deterioration. In one aspect, a method includes irradiating a lubrication oil sample with a light beam to emit a light-induced fluorescence, detecting and processing the light-induced fluorescence signal to determine a temporal variation of a fluorescence intensity, identifying a steady state of the light-induced fluorescence signal, processing the temporal variation of the fluorescence intensity to determine a lubrication oil parameter, and correlating the oil parameter to a calibration curve to diagnose the lubrication oil deterioration.

8 Claims, 5 Drawing Sheets

(51) Int. Cl.
*G01J 3/44* (2006.01)
*G01J 3/46* (2006.01)
*G01N 21/64* (2006.01)

(52) U.S. Cl.
CPC ....... *G01N 21/6402* (2013.01); *G01N 21/643* (2013.01); *G01N 21/6408* (2013.01); *G01N 2021/6482* (2013.01); *G01N 2201/129* (2013.01)

(58) Field of Classification Search
CPC .. G01N 33/00; G01N 21/314; G01N 21/3577; G01N 21/6408; G01N 2011/008; G01N 21/15; G01N 21/43; G01N 2291/0258; G01N 29/02
USPC .......................................................... 250/301
See application file for complete search history.

(56) References Cited

U.S. PATENT DOCUMENTS

| | | | |
|---|---|---|---|
| 5,422,719 A | 6/1995 | Goldstein | |
| 5,818,582 A | 10/1998 | Fernandez et al. | |
| 5,982,847 A * | 11/1999 | Nelson | G01N 33/2858 378/45 |
| 6,023,961 A * | 2/2000 | Discenzo | F16C 19/52 422/68.1 |
| 6,507,401 B1 * | 1/2003 | Turner | E21B 47/102 356/417 |
| 6,525,325 B1 | 2/2003 | Andrews et al. | |
| 6,707,556 B2 * | 3/2004 | Turner | E21B 47/102 250/458.1 |
| 7,442,291 B1 * | 10/2008 | Discenzo | B01D 35/143 210/443 |
| 8,390,796 B2 * | 3/2013 | Honda | G01N 21/27 356/71 |
| 8,704,174 B2 * | 4/2014 | Ukon | G01N 21/6408 250/301 |
| 2002/0158211 A1 | 10/2002 | Gillispie | |
| 2003/0133105 A1 | 7/2003 | Gorelik et al. | |
| 2003/0141459 A1 * | 7/2003 | Hegazi | G01N 21/6408 250/461.1 |
| 2004/0007675 A1 | 1/2004 | Gillispie et al. | |
| 2004/0124366 A1 | 7/2004 | Zeng et al. | |
| 2006/0114007 A1 * | 6/2006 | Cho | G01N 33/2888 324/698 |
| 2007/0063140 A1 * | 3/2007 | Liu | G01N 15/0205 250/301 |
| 2007/0095395 A1 * | 5/2007 | Spiess | F16N 29/02 137/246 |
| 2007/0187617 A1 * | 8/2007 | Kong | G01N 21/6408 250/461.1 |
| 2009/0006004 A1 | 1/2009 | Sens et al. | |
| 2011/0155925 A1 * | 6/2011 | Ukon | G01N 21/6408 250/458.1 |
| 2011/0166802 A1 * | 7/2011 | Kong | G01N 11/10 702/50 |
| 2011/0236569 A1 * | 9/2011 | Weiller | B23K 26/123 427/162 |
| 2011/0267603 A1 * | 11/2011 | Shaw | G01N 21/431 356/128 |
| 2011/0303834 A1 | 12/2011 | Hegazi et al. | |
| 2012/0086942 A1 * | 4/2012 | Honda | G01N 21/27 356/436 |
| 2013/0333893 A1 * | 12/2013 | Morris | E21B 43/128 166/312 |
| 2014/0198313 A1 | 7/2014 | Tracy et al. | |
| 2015/0009495 A1 | 1/2015 | Li et al. | |
| 2015/0085290 A1 * | 3/2015 | Fjerdingstad | G01N 1/2035 356/445 |
| 2016/0195509 A1 * | 7/2016 | Jamieson | G01N 33/2858 356/70 |
| 2016/0202194 A1 * | 7/2016 | Lees | G01N 23/223 378/47 |
| 2016/0349198 A1 * | 12/2016 | Barney | G01N 23/223 |

OTHER PUBLICATIONS

Wronski et al., "The step response: a method to characterize mechanisms of renal blood flow autoregulation," American Journal of Physiology—Renal Physiology, Sep. 3, 2003, vol. 285 No. 4; pp. F758-F764.

Schuresko et al., "Carboxylation kinetics of hemoglobin and myoglobin: linear transient response to step perturbation by laser photolysis," Biophysical Journal, vol. 24, No. 1, Oct. 1978; pp. 382-383, <http://dx.doi.org/10.1016/S0006-3495(78)85390-9>.

Petermann, "Chapter 4: Intensity-Modulation Characteristics of Laser Diodes," Laser diode modulation and Noise, Kluwer Academic, 1991, 78-118.

Mendonca et al., "Application of step response impedance spectroscopy for detection of skin irritation," Engineering in Medicine and Biology Society, Sep. 17-21, 2003; Proceedings of the 25th Annual International Conference of the IEEE, vol. 4; pp. 3215-3217.

Bridges et al., "Small-signal step response of laser amplifiers and measurement of CO2 laser linewidth," IEEE Journal of Quantum Electronics, Nov. 1968, vol. 4, No. 11; pp. 777-782.

Zhang et al., "Spray model based on step response theory," Fuel, May 2012, vol. 95, No. 1; pp. 499-503, <http://dx.doi.org/10.1016/j.fuel.2011.12.037.

Rowland et al., "The Automated Assessment of Ultrasound Scanner Lateral and Slice Thickness Resolution: Use of the Step Response," Ultrasound in Medicine & Biology, Sep. 2009, vol. 35, No. 9; pp. 1525-1534, http://dx.doi.org/10.1016/j.ultrasmedbio.2009.03.015.

Fiorentin et al., "Effect of the finite memory length of a recorder in evaluating its frequency response of from step response," Instrumentation and Measurement Technology Conference, May 21-23, 2002; Proceedings of the 19th IEEE, vol. 1; pp. 787-791.

Wardzinska et al., "Step response sensitivity of VLSI interconnects," 17th IEEE Workshop on Signal and Power Integrity (SPI), May 12-15, 2013; pp. 1-4.

Aboaba et al., "Brain tumor quantification equation: Modeled on complete step response algorithm," International Conference on Computer and Communication Engineering (ICCCE 2012), Jul. 3-5, 2012; pp. 988-991.

Bieler et al., "Calibration of the step response of a 70 GHz sampling oscilloscope using a novel optoelectronic technique," Conference on Precision Electromagnetic Measurements Digest, CPEM Jun. 8-13, 2008; pp. 678-679.

Yamagata et al., "Synthesis of highly fluorescent diketopyrrolopyrrole derivative and two-step response of fluorescence to acid," Tetrahedron Letters, Mar. 24, 2010, vol. 51, No. 12; pp. 1596-1599 http://dx.doi.org/10.1016/j.tetlet.2010.01.069.

International Search Report and Written Opinion of the International Searching Authority issued in International Application No. PCT/US2017/029456 dated Jul. 10, 2017; 14 pages.

\* cited by examiner

CHARACTERIZING LUBRICANT OIL DEGRADATION USING FLUORESCENCE SIGNALS

CROSS-REFERENCE TO RELATED APPLICATION(S)

This application claims the benefit of priority to U.S. Provisional Patent Application Ser. No. 62/327,558, filed on Apr. 26, 2016, the contents of which are hereby incorporated by reference.

TECHNICAL FIELD

This specification relates to lubrication oil analysis (LOA) and related methods.

BACKGROUND

Lubrication oil performs two essential tasks. One is to provide a homogenous protective layer between surfaces that are in relative motion to reduce friction, prevent wear and avoid the catastrophic event of seizure resulting from mating parts. Another role of lubrication oil is to maintain working parts cool, protect against corrosion and flush away contaminants and deposits for the surface of mating parts. Lubrication oil degradation is caused by several factors that include: variation in the electrical, physical, chemical, and optical properties. The main causes for the deterioration are a combination of water contamination, oxidation and particle contamination. Several parameters can be used to monitor the degradation of lubrication oil, such as viscosity, water content, total acid number (TAN), total base number (TBN), particle counting, pH value or others. Other parameters, that correlate well with the standard parameters, such as viscosity measurements, can also be used to identify varying grades of degradation from real samples of oils.

Lubrication oil analysis (LOA) is a process used to derive oil analysis data (for example, physical and chemical properties) from lubrication oil samples obtained from industrial equipment. The industrial equipment can contain rotating and moving parts (for example, gear boxes, hydraulic systems, engines, compressors, turbines or other moving parts), such as equipment used in hydrocarbon-producing wells. LOA can reveal viscosity changes, as well as ferrous and nonferrous contamination. LOA can also indicate corrosion of the equipment, leaks between different parts of the equipment, remedial actions, or other critical machinery diagnostic information. LOA can provide information about the useful lifetime of the lubrication oil along with the status of the lubrication oil. Knowledge of the useful lifetime and the status of the lubrication oil can be used to ensure the reliability and correct functioning of the equipment.

SUMMARY

The present disclosure describes methods and systems for performing lubrication oil analysis (LOA) of a lubrication oil sample. In some implementations, a method includes irradiating a lubrication oil sample with a light beam such that a light-induced fluorescence can be emitted from the lubrication oil sample, detecting a light-induced fluorescence signal from the lubrication oil sample, processing the light-induced fluorescence signal to determine a temporal variation of a fluorescence intensity, identifying a steady state of the light-induced fluorescence signal based on the temporal variation of the fluorescence intensity, after identifying the steady state, processing the temporal variation of the fluorescence intensity to determine a lubrication oil parameter, and correlating the oil parameter to a calibration curve to diagnose the lubrication oil deterioration.

The foregoing and other implementations can each optionally include one or more of the following features, alone or in combination. In an aspect, the method includes collecting the lubrication oil sample from an industrial equipment. The light beam can be a continuous electromagnetic wave characterized by a single wavelength. The single wavelength can be between 200 nanometers and 550 nanometers.

In a further aspect, the method includes converting the continuous electromagnetic wave into a plurality of step light beams, such that each step light beam has substantially the same intensity within a time interval. The method can further include guiding the light beam at an acute angle on a front surface of a container holding the lubrication oil sample. The method can further include filtering the light-induced fluorescence signal.

In a further aspect, the method includes capturing the light-induced fluorescence signal by a fast photodiode. The fluorescence intensity can be represented as a second order dynamic system. The oil parameter can be associated to an oil viscosity. The oil parameter can be a damping factor of the fluorescence signal. The second order dynamic system corresponds to an over-damped oscillator and the damping factor can be larger than 1. The oil parameter can be an undamped natural frequency of the fluorescence signal. The second order dynamic system corresponds to an under-damped oscillator and the damping factor can be smaller than 1.

In a further aspect, the method includes comparing the oil parameter to previously measured oil parameter to determine an oil deterioration rate. The method can further include determining an estimate of a useful remaining lifetime of the industrial equipment associated to the lubrication oil sample based on the oil deterioration rate. The industrial equipment can be in use in a hydrocarbon-producing well during determining the estimate of the useful remaining lifetime of the industrial equipment. The industrial equipment can be a submersible pump configured to pump fluid uphole from the hydrocarbon-producing well and wherein the submersible pump can be disposed within the hydrocarbon-producing well. In a further aspect, the light beam can be generated by a laser source.

In some implementations, the present disclosure also provides a non-transitory, computer-readable medium for diagnosing lubrication oil deterioration and storing computer-readable instructions. The instructions can be executable by a computer and the non-transitory, computer-readable medium can be configured to: guide a light beam to a lubrication oil sample, detect light-induced fluorescence signal from the lubrication oil sample, process the light-induced fluorescence signal to determine a temporal variation of a fluorescence intensity, identify a steady state of the light-induced fluorescence signal based on the temporal variation of the fluorescence intensity, process the temporal variation of the fluorescence intensity to determine a lubrication oil parameter, and correlate the oil parameter to a calibration curve to diagnose lubrication oil deterioration.

In some implementations, the present disclosure also provides a system to diagnose lubrication oil deterioration, the system including: a memory and a hardware processor interoperably coupled with the memory. The hardware processor can be configured to: guide a light beam to a lubrication oil sample, detect light-induced fluorescence signal from the lubrication oil sample, process the light-induced fluorescence signal to determine a temporal variation of a fluorescence intensity, identify a steady state of the light-induced fluorescence signal based on the temporal variation of the fluorescence intensity, process the temporal variation of the fluorescence intensity to determine a lubrication oil parameter, and correlate the oil parameter to a calibration curve to diagnose lubrication oil deterioration.

In some implementations, the present disclosure also provides another system to diagnose lubrication oil deterioration, the system including: a light beam generator configured to generate a light beam, a container including a lubrication oil sample, an optical equipment configured to guide the light beam to a face of the container, a fast photodiode configured to detect light-induced fluorescence signal from the lubrication oil sample, and a hardware processor interoperably coupled with a memory. The hardware processor can be configured to: process the light-induced fluorescence signal to determine a temporal variation of a fluorescence intensity, identify a steady state of the light-induced fluorescence signal based on the temporal variation of the fluorescence intensity, process the temporal variation of the fluorescence intensity to determine a lubrication oil parameter, and correlate the oil parameter to a calibration curve to diagnose lubrication oil deterioration.

The details of one or more implementations of the subject matter of this specification are set forth in the accompanying drawings and associated description. Other features, aspects, and advantages of the subject matter will become apparent from the description, the drawings, and the claims.

DETAILED DESCRIPTION

Figure 1:
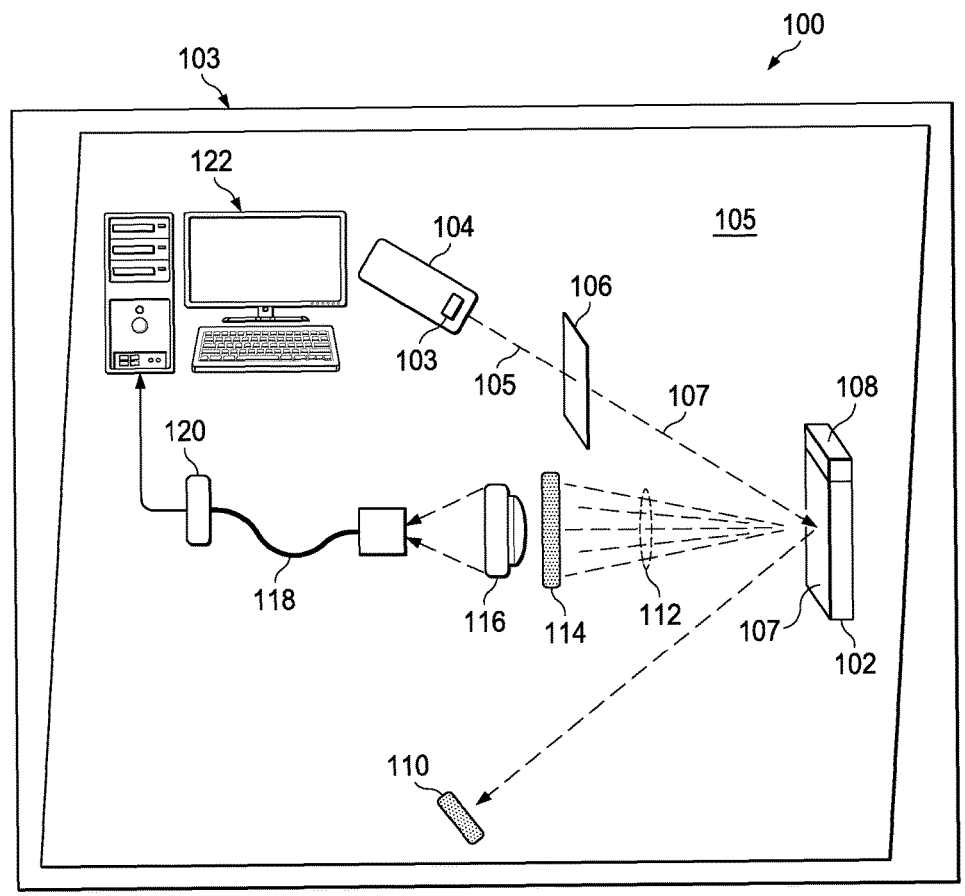
FIG. 1 is a diagram illustrating an example system for characterizing lubricant oil degradation using fluorescence signals.

Currently, the condition of lubrication oil provides the best possible detection method for early warning of machine failure. However, the majority of industries use offsite and offline lubrication oil analysis (LOA) to quantify the remaining lifetime of the oil. It would be beneficial to have an accurate, efficient, and rapid ability to perform onsite LOA.

LOA is a process used to derive one or more characteristics (for example, physical and chemical properties) of a lubrication oil, such as lubrication oil samples obtained from equipment used in hydrocarbon-producing wells. LOA is typically performed offsite and offline. In some cases, each lubrication oil sample can require a day or more to fully analyze before one or more of the electrical, physical, chemical, and optical properties can be determined. Changes over time in the LOA in lubrication oil samples from one or more pieces of equipment used in hydrocarbon-producing wells can provide data useful to determine the operational lifetime trends of the equipment. The normal practice for comparing and validating available lubrication oil analysis data is to leverage technical skill or expertise to numerically interpret lubrication oil analysis data, but does not leverage correlations or relationships that can be efficiently derived from available lubrication oil analysis data and rapid measurement of lubrication oil characteristics. It is important to have an efficient, rapid, and simple ability to derive up-to-date data based on prior LOA lubrication oil analysis data in order to be able to perform special analysis studies and to determine, for example and among other things, the earlier-mentioned hydrocarbon resource trends and reduction or increase of lubrication oil degradation.

At a high level, this disclosure generally describes methods and systems, including computer-implemented methods, computer program products, and computer systems, for predicting lubrication oil degradation of a lubrication oil sample obtained from an equipment used in a hydrocarbon well. Particularly, the predictions are based on determining a damping factor or an undamped natural frequency or both, of a fluorescence signal generated by the lubrication oil sample, which are directly proportional to the viscosity of the lubricant oil sample. The subject matter described in this specification can be implemented in particular implementations so as to realize one or more of the following advantages. The methods and the systems described in this specification can be implemented to diagnose oil degradation in the proximity of a hydrocarbon well, on a regular basis, such as a daily basis, at low costs, non-intrusively and on-line. LOA data can be obtained for a lubrication oil sample from a particular hydrocarbon well equipment, such as turbine oil. LOA can include physical properties, such as lubrication oil viscosity, which can be leveraged by applications to provide useful analysis and predictive functions of equipment lifetime. LOA can be performed using minimum amounts of lubrication oil (for example, turbine oil) for analysis (for example, 1-2 milliliters).

In some implementations, LOA can be used to automatically predict a quantitative value of the remaining useful lifetime of the analyzed lubrication oil sample. The use of LOA is an easy, efficient, and time saving process of comparing and validating available LOA lubrication oil analysis data. LOA can be associated to multiple performed actions that include determination of lubrication oil breakthrough, determination of lubrication oil invasion, determination of casing leaks between two hydrocarbon reservoirs, prediction of scale precipitation, monitoring sweep, performing remedial or proactive actions based on LOA lubrication oil analysis data correlations, predictions, or other performed actions. LOA can enhance the efficiency of the performed actions based on LOA lubrication oil analysis data that can be derived or predicted from rapid and simple measurement of lubrication oil fluorescence. Multiple oil samples extracted from the same equipment at different times (for example, during a time interval in which the lubricant oil of an equipment was not replenished or replaced) can be used to generate a graphical correlation of respective LOAs. The graphical correlation of multiple LOAs can provide data useful for monitoring and adjusting development of specific hydrocarbon-wells or groups of wells, -plants, -fields, or -reservoirs. For example, the described approach for correlating or relating, displaying, and predicting data pertaining to LOAs can be used by one or more elements of an organization to develop different actions particular to their assigned function for the organization.

FIG. 1 is a diagram illustrating an example of a system 100 provided by the present disclosure. The system 100 of FIG. 1 can be used to perform LOA and to derive the damping factor or an undamped natural frequency of a fluorescence signal generated by the analyzed lubrication oil sample 102. In some implementations, the system 100 is covered by a housing 103, which provides access to the container 108 holding the lubrication oil sample 102. All components or some components of the system 100 can be attached to a supporting fixture 105 (for example, a table, a shelf, a frame or any other type of supporting fixture). The example components of the system 100 can include a laser source 104, a chopper 106, a container 108, a beam dump 110, an optical filter 114, lenses 116, a fiber optic 118, a fast photodiode 120 and a computing system 122.

In some implementations, the laser source 104 can generate a light beam as continuous electromagnetic waves 105. The laser source 104 can emit electromagnetic waves 105 of a single wavelength (for example, laser beam). In some implementations, the laser source 104 can be a tunable laser that can emit electromagnetic waves 105 of a plurality of wavelengths within a range of wavelengths. In some examples, the laser source 104 can include a polarizing filter 103 that polarizes the electromagnetic waves 105 that are directed towards the lubrication oil sample 102. The laser source 104 can include a set of one or more reflectors that varies the angle at which the electromagnetic waves 105 are delivered from the laser source 104. In some examples, the angle at which a laser beam is oriented can be adjusted. The electromagnetic waves 105 can be in the visible light spectrum, in the ultraviolet light spectrum, or in the infrared light spectrum. For example, the wavelengths of the electromagnetic waves 105 can be within a range of 200-550 nanometers.

In some implementations, the laser source 104 can be a continuous wave (CW) collimated laser with a central emission wavelength of 405 nanometers and output power of 20 milliwatts. In some implementations, the laser source 104 can be a pulsed-wave laser. The laser source 104 is aligned such that it generates a laser beam incident on the front surface of the container 108 (for example, at an angle of 45 degrees to the plane of the surface in the horizontal direction). The chopper 106 can be a mechanical optical chopper. The chopper 106 can be placed in the optical path of the collimated laser beam 105, before the container 108. The chopper 106 can open quickly and remain open for a predetermined period of time. For example, the chopper 106 can convert the continuous laser beam 105 into a step laser beam 107 with a constant intensity for a particular time interval (for example, 4 minutes or a longer or shorter time duration). A part of the step laser beam 107 is reflected by the walls of the container 108. The reflected laser beam can be absorbed by a beam dump 110.

The step laser beam 107 crosses the walls of the container 108 to irradiate the lubrication oil sample 102. The container 108 has walls that are transparent to the central emission wavelength (for example, 405 nanometers). For example, the container 108 can be a quartz cuvette. The container 108 can have multiple geometries that provide at least one planar side (for example, a planar front wall 107) that enables optimization of the irradiation of the lubricant oil. For example, the container 108 can be square-shaped or rectangular shaped. The lubrication oil sample 102, irradiated by the step laser beam 107, generates a laser-induced fluorescence signal 112. The fluorescence signal 112 of the lubricant oil is filtered by the optical filter 114, which is placed parallel to the front wall 107 of the container 108 that is first crossed by the electromagnetic waves generated by the laser 104 (for example, front surface of the container 108). The center of the optical filter 114 is aligned with the incidence point of the step laser beam 107 and the front wall 107 of the container 108.

The broadband fluorescence spectrum emission signal (plus or minus 200 nanometers) can be optically filtered using the optical filter 114, having a narrow wavelength range (plus or minus 10 nanometers). For example, the fluorescence signal 112 can be filtered by the optical filter 114 at one wavelength, which is chosen to correspond to a fluorescence signal of a reasonable intensity (for example, 440 plus or minus 10 nanometers). The filtered fluorescence signal 112 can be collimated and focused by lenses 116 onto an optical fiber 118. The optical fiber 118 can be connected to a fast photodiode 120 to capture the fluorescence intensity as function of time. The output signal of the photodiode 120 at the filtered wavelength (for example, 440 plus or minus 10 nanometers) can be acquired and recorded every 20 ms during the time interval, in which the chopper is open.

The acquired fluorescence signal can be processed by a computing system 122. Data post processing can include smoothing, reduction of redundant information and fitting algorithms (for example, process 200 described with reference to FIG. 2). In some implementations, the computing system 122 can be a mobile handheld device. In some examples, the computing system 122 and the laser source 104 can be directly connected to and powered by an external power source (for example, a wall outlet).

In some implementations, the computing system 122 can include a trigger source that is a computer program operable to control one or more of a start time, an end time, and a rate at which the chopper 106 opens and closes. In some examples, the trigger source can be determined by an algorithm stored within a computer-readable memory of the computing system 122. In some implementations, the system 100 can include a trigger source that is housed external to and separately from the computing system 122 or affixed to the external surface of the chopper 106. For example, the trigger source can be a foot pedal, a switch, a button, or a lever that allows a user of the system 100 to activate the trigger source by depressing the pedal, flipping the switch, depressing the button, or moving the lever, respectively. In some examples, the trigger source is operable to cause the chopper 106 to deliver a laser beam with a particular temporal characteristic to the lubrication oil sample 102 when the trigger source is activated by the user of the system 100.

Figure 2:
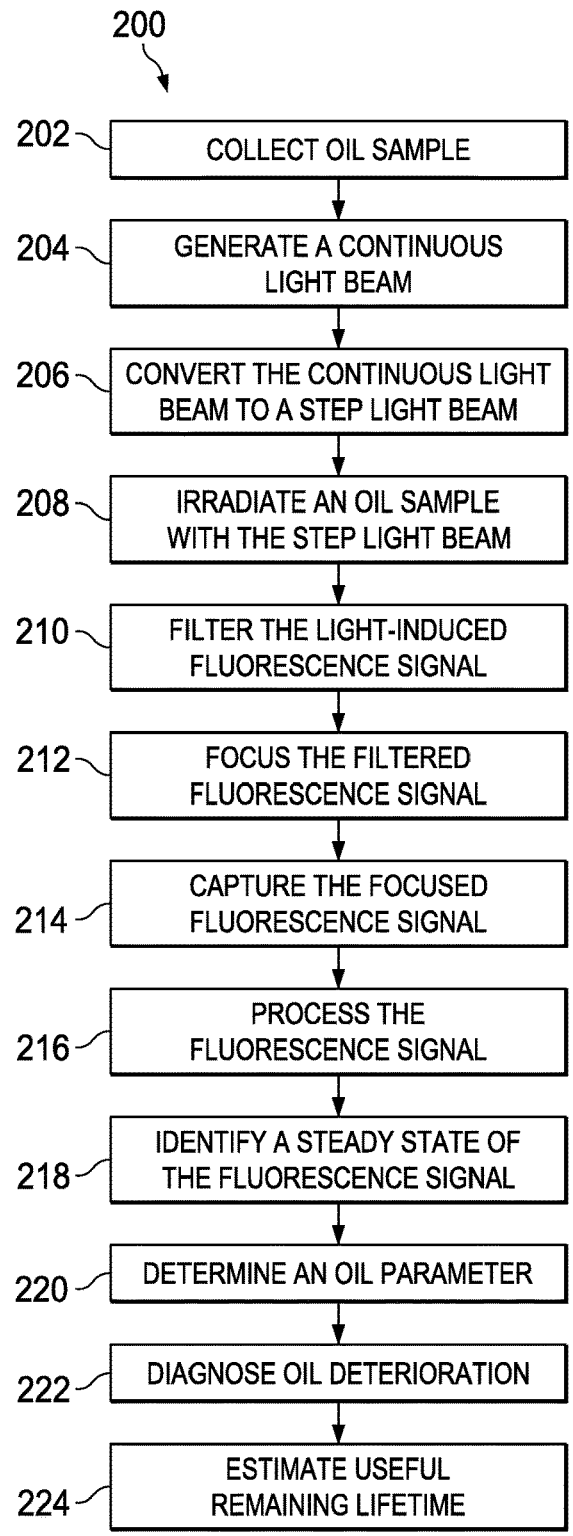
FIG. 2 is a flow chart of an example of a process for characterizing lubricant oil degradation using fluorescence signals.

FIG. 2 is a flow chart of a method 200 for diagnosing oil deterioration according to an implementation. The method 200 can be executed using the systems described with reference to FIGS. 1 and 5, in the proximity of a hydrocarbon well. However, it will be understood that method 200 can be performed, for example, by any other suitable system, environment, software, and hardware, or a combination of systems, environments, software, and hardware as appropriate. In some implementations, various steps of method 200 can be run in parallel, in combination, in loops, or in any order.

At 202, an oil sample is collected. The oil sample can be a lubricant oil sample that is collected from an equipment used in a hydrocarbon well for LOA. The amount of collected oil sample can be smaller than 1 centiliters (for example, about 1-2 milliliters). The collection of the oil sample can include placing the oil sample in an optically transparent cuvette. The cuvette can be a quartz cuvette with 1 cm optical path length.

At 204, a light beam is generated. The light beam can be an electromagnetic wave of a particular wavelength. For example, the light beam can be a CW laser radiation. The laser source used to generate the CW laser radiation can be a CW collimated laser with a central emission wavelength of 405 nanometers and output power of 20 milliwatts. The laser can be setup so that it is incident on the front surface of the cuvette and at a preferred incidence angle (for example, 45 degrees) to the plane of the surface in the horizontal direction. In some implementations, the laser can be setup in a position that is independent from the front surface of the cuvette and the light beam is directed towards the front surface of the cuvette at a preferred incidence angle through an optical system made of one or more lenses and mirrors.

At 206, the continuous light beam is converted into a step light beam. The conversion to step light beam can be done by a mechanical optical chopper placed in the path of the collimated laser beam, before the cuvette (see FIG. 1). The mechanical optical chopper can provide a step laser intensity on the sample for a particular time interval (for example, 4 minutes). At 208, the oil sample is irradiated by the step light beam. At 210, the resulting laser-induced fluorescence signal from the lubricant oil is optically filtered by an optical filter. For example, the fluorescence signal can be optically filtered at one wavelength corresponding to a fluorescence signal of reasonable intensity (for example, 440 plus or minus 10 nanometers). At 212, the filtered fluorescence signal can be collimated and focused onto an optical fiber, using a combination of lenses.

At 214, the fluorescence signal can be captured by a fast photodiode as function of time. The fast photodiode can be synchronized to the mechanical optical chopper, such that the fluorescence signal is captured while the mechanical optical chopper is open. For example, the photodiode can acquire and record the fluorescence signal every 20 ms once the mechanical optical chopper is open.

At 216, the fluorescence signal is processed. Data processing can include smoothing, reduction of redundant information and fitting algorithms. Fitting algorithms are based on the type of oil that is analyzed. Each type of oil is associated to a particular temporal variation of the fluorescence intensity. For example, some oils do not produce a damping effect. In case no damping effect is produced, the natural frequency can be measured. Some oil samples produce an overdamped effect. In case an overdamped effect is produced, the natural frequency or the damping factor (>1) or both can be measured. And a third type of oils produce underdamped behavior, in which the natural frequency or the damping factor (<1) or both can be used. For determining a damping factor, the fluorescence signal is treated as a second order system. An example second order differential equation that can be used to describe the behavior of the second order fluorescence response is:

$$\ddot{x}+2\zeta\omega_n\dot{x}+\omega_n^2 x=f(t) \tag{Eq. 1}$$

In Eq. 1, x is the response of the system, in this case the time-dependent fluorescence response of the oil, $\omega_n$ is the un-damped natural frequency during the transient response, $\zeta$ is the damping factor of the fluorescence response and f(t) is the applied function to the system, in this case the incident laser radiation.

To examine the transient response of the induced fluorescence signal a unit step function u(t) can be applied to represent the sudden onset of the laser:

$$f(t) = u(t) = \begin{cases} 0 \text{ for } t < 0 \\ 1 \text{ for } t \geq 0 \end{cases} \tag{Eq. 2}$$

In Eq. 2, for time<0, the laser is off, and for time≥0, the laser is on, in continuous wave mode. Accordingly the second order differential equation for the time-dependent fluorescence response (Eq. 1) becomes:

$$\ddot{x}+2\zeta\omega_n\dot{x}+\omega_n^2 x=u(t) \tag{Eq. 3}$$

In Eq. 3, u(t) is the previously described step function.

At 218 a steady state of the light-induced fluorescence signal is identified based on the temporal variation of the fluorescence intensity. The steady state value of the light-induced fluorescence signal can indicate if the time-dependent fluorescence response corresponds to an over damped system or a critically damped system. In some implementations, the time-dependent fluorescence response corresponds to an over damped system. In the case of an over damped system, the damping factor is greater than one ($\zeta$>1) the over-damped step response can be expressed as:

$$x(t) = \frac{1}{\omega_n^2}\left[1 + \frac{1}{2\sqrt{1-\zeta^2}}\left(\frac{1}{-\zeta+\sqrt{\zeta^2-1}}e^{-\omega_n(\zeta-\sqrt{\zeta^2-1})t} + \frac{1}{\zeta+\sqrt{\zeta^2-1}}e^{-\omega_n(\zeta+\sqrt{\zeta^2-1})t}\right)\right] \tag{Eq. 4}$$

Eq. 4 is the solution of the damped equation for the over-damped case system response, where all the initial conditions are assumed to be zero.

In some implementations, the time-dependent fluorescence response corresponds to a critically damped system. The solution of Eq. 2 for the critically damped case, in which the damping ratio is equal to one ($\zeta$=1), is expressed as follows:

$$x(t) = \frac{1}{\omega_n^2}[1 - e^{-\omega_n t}(1 - \omega_n t)] \tag{Eq. 4'}$$

In Eq. 4' all the initial conditions are assumed to be zero.

At 220, after the identification of the steady state, an oil parameter is determined. The oil parameter can include the damping factor and the undamped natural frequency of the fluorescence signal. For example, the results of the analysis of the temporal response of the laser induced fluorescence of lubrication oil as a second order system (including a steady state phase) can be used to provide the oil parameter associated to the over-damped or undamped natural frequency of the response. In particular, the damping ratio can be used as a parameter for oil characterization. In some implementations, the determined oil parameter values are displayed to a user analyzing the oil sample and stored in a suitable persistent memory storage, such as a database. Steps 202 to 220 can be repeated for multiple samples (including a fresh sample and deteriorated samples) of the same type of oil, extracted at different times from a particular equipment.

At 222, the oil parameter is used to determine the degradation of the oil. At 224, the degradation of the oil is used to determine the useful remaining lifetime of the oil (for example, days, weeks, months or years). The useful remaining lifetime of the oil can be determined by correlating the change in the measured damping factor or the natural frequency to the calibration curve for each type of oil. For a particular type of oil, the damping factor or the undamped natural frequency of the fluorescence signal of one fresh sample can be compared to the corresponding parameters of multiple deteriorated samples of the same oil type. For those oils that produce a damping effect, the damping factor of the fresh sample (for example, 1.26 radians/second) can be used as a reference point and as the value of the damping factor increases above the corresponding threshold (for example, 3.3 radians/second) it can indicate that the oil is degraded beyond use and replacement is recommendable. For those oils that are characterized by an underdamped behavior, the natural frequency of a fresh sample of one type of lubrication oil (for example, 3.36 radians/second) can be used as a reference point for the corresponding type of lubrication oil. A value of the natural frequency that exceeds a particular threshold (for example, 8.5 radians/second) can indicate that the oil is degraded beyond use and replacement is recommendable. In some implementations, the estimated useful remaining lifetime of the oil is provided (for example, displayed) to a user analyzing the oil sample and stored in a suitable persistent memory storage. In some implementations, the results of the process 200 are stored in sets corresponding to each equipment associated to the tested oil degradation. The records can be used to find the rate of increase in the natural frequency or in the damping factor for each equipment and convert the degradation rate into the estimate of the useful remaining lifetime. The determined LOA data (for example, oil parameter) can be stored as a backup in any suitable persistent memory storage, such as a database. For example, in some implementations, the backup data can be stored in an offsite data repository, in a separate local or remote database, or within a machine associated database.

The use of any suitable programming language is considered to be within the scope of this disclosure. LOA lubrication oil analysis data can be retrieved (for example, using a suitable database query language) from earlier database to determine a degradation rate. Processing can include a repetition of steps 202-224 at different times (corresponding to different degradation rates) and an estimated useful remaining lifetime of the oil is provided (for example, displayed). Output of the method 200 can be provided in a standard tabular format, but other formats are possible and considered to be within the scope of this disclosure.

The method 200 can be used to determine relationships between the LOA parameters (for example, natural frequency or the damping factor) associated with the existing LOA lubrication oil analysis data (for example, viscosity) and then graphically display the determined relationship results using a graphical technique, as described with reference to FIGS. 3B and 4B.

Figure 3A:
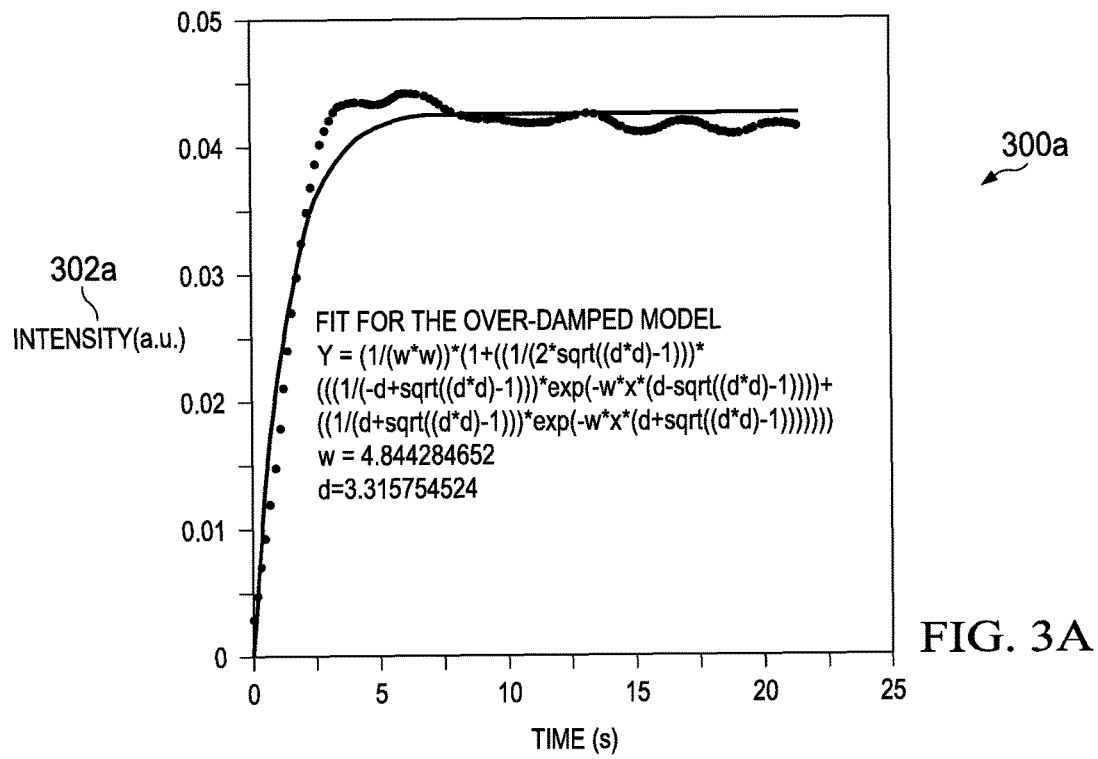
FIGS. 3A and 3B illustrate example plots of data associated with an over-damped model of oil samples according to an implementation.

FIG. 3A illustrates an example fit for the over-damped model corresponding to an oil sample 300a. Fluorescence intensity 302a is displayed as a function of time with a selected time resolution (for example, 20 ms). The term w corresponds to the best fit frequency in radians/second and d is the damping factor. In some implementations, a similar graph can be displayed to a user analyzing a particular oil sample, according to method 200. The example display can allow a rapid, visual analysis of the presented data.

Figure 3B:
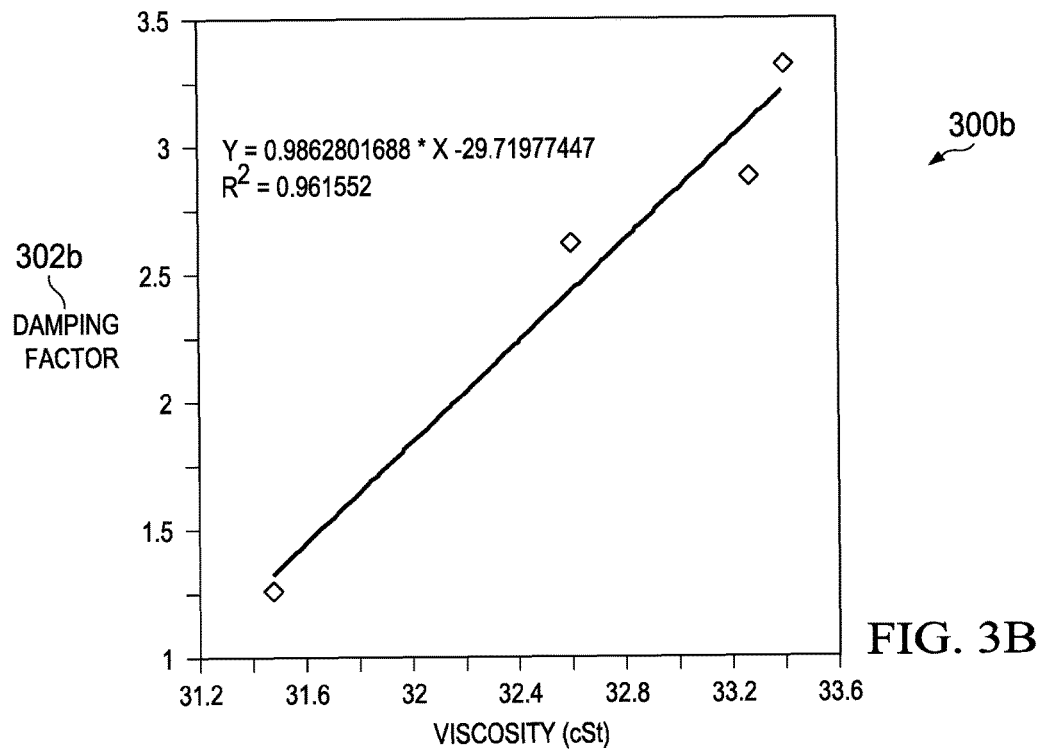

FIG. 3B illustrates an example experimental validation 300b of method 200 for an over-damped system, described with reference to FIG. 2. The experimental validation tests the relationship between damping factors 302b determined using method 200 and kinematic viscosities for a plurality of oil samples. Experimental validation tests were performed on 4 different samples of turbine lubricant oils taken from the same equipment, at different times (for example, corresponding to different levels of deterioration). The kinematic viscosity (at 40° C.) and density (at 20° C.) were measured using ASTM D-7024 and D-4052, respectively, and are listed in Table 1. Data reduction algorithm was used to reduce the number of points by 5 times before a best fit for Eq. 4 was carried out to obtain the oscillation frequency for each of the samples. The damping factor of the oils tested was found to increase with viscosity. A plot of the oscillator frequency vs. viscosity, as shown in FIG. 3B shows a linear correlation of $R^2$ values (for example, coefficient of determination) better than 96%. The linear correlation between the oil parameter and viscosity, as illustrated in FIG. 3B indicates that method 200 can be used to measure the deterioration condition of the lubricant oil. The relationship between the damping factor, density and kinematic viscosity can also be used to determine the viscosity of turbine oil in-situ for each analyzed oil sample.

TABLE 1

|  | Density at 20° C. | Kinematic viscosity at 40° C. |
| --- | --- | --- |
| Sample 1 | 0.8739 | 31.476 |
| Sample 2 | 0.8716 | 32.605 |
| Sample 3 | 0.8737 | 33.243 |
| Sample 4 | 0.8737 | 33.270 |

Figure 4A:
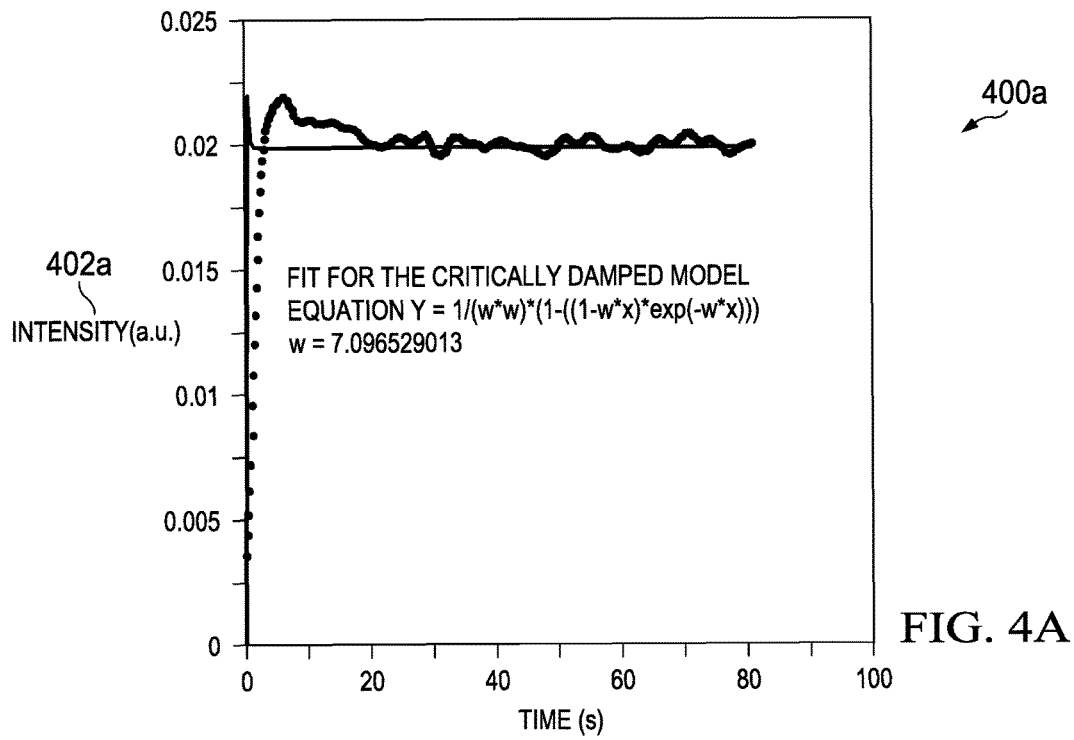
FIGS. 4A and 4B illustrate example plots of data associated with a critically damped model of oil samples according to an implementation.

FIG. 4A illustrates an example fit for the critically-damped model corresponding to an oil sample 400a. Fluorescence intensity 402a is displayed as a function of time with a selected time resolution (for example, 20 ms). The term w corresponds to the best fit fluorescence oscillation frequency in radians/second. In some implementations, a similar graph can be displayed to a user analyzing a particular oil sample, according to method 200. The example display can allow a rapid, visual analysis of the presented data.

Figure 4B:
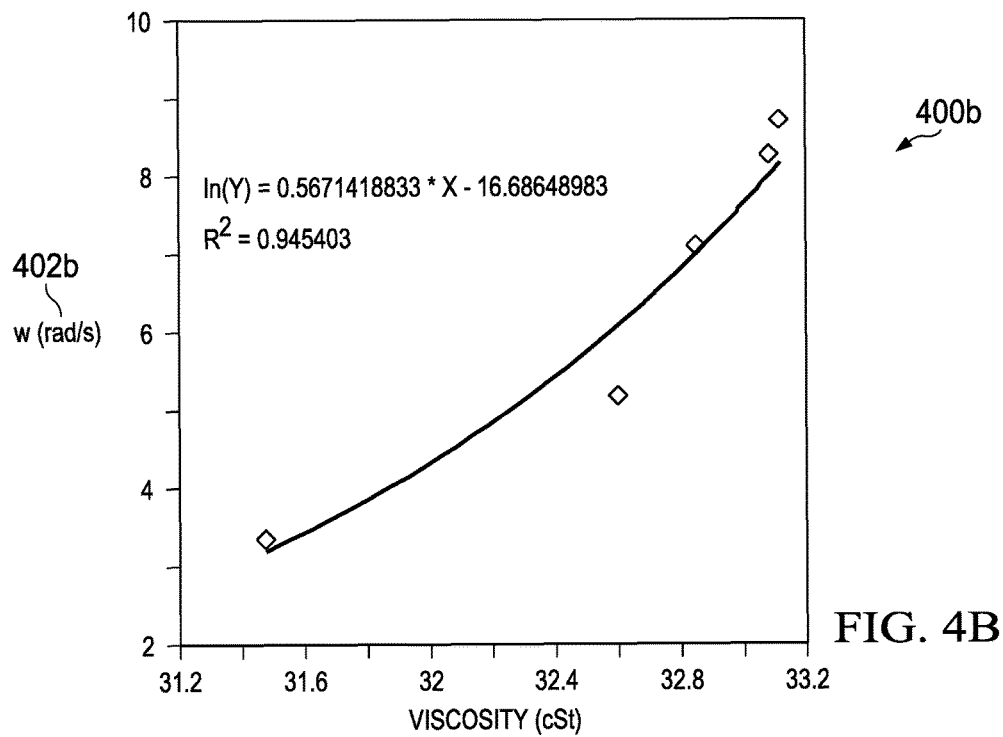

FIG. 4B illustrates an example experimental validation 400b of method 200 for a critically damped system, described with reference to FIG. 2. The experimental validation tests the relationship between undamped natural frequencies (expressed in radians/second) 402b determined using method 200 and kinematic viscosities for a plurality of oil samples. Experimental validation tests were performed on 5 different samples of turbine lubricant oils taken from the same equipment, at different times (for example, corresponding to different levels of deterioration). The kinematic viscosity (at 40° C.) and density (at 20° C.) were measured using ASTM D-7024 and D-4052, respectively, and are listed in Table 2.

TABLE 2

|  | Density at 20° C. | Kinematic viscosity at 40° C. |
| --- | --- | --- |
| Sample 1 | 0.8739 | 31.476 |
| Sample 2 | 0.8716 | 32.605 |
| Sample 3 | 0.8723 | 32.850 |
| Sample 4 | 0.8739 | 33.084 |
| Sample 5 | 0.8739 | 33.122 |

Data reduction algorithm was used to reduce the number of points by 5 times before a best fit for Eq. 4' was carried out to obtain the oscillation frequency for each of the samples. The fluorescence oscillation frequencies of the tested oils were found to increase with viscosity. A plot of the oscillator frequency vs viscosity is shown in FIG. 4B, which shows a logarithmic correlation of $R^2$ values (for example, coefficient of determination) better than 94%. The linear correlation between the oil parameter and viscosity, as illustrated in FIG. 4B indicates that method 200 can be used to measure the deterioration condition of the lubricant oil. The relationship between the undamped natural frequency, density and kinematic viscosity can also be used to determine the viscosity of turbine oil in-situ for each analyzed oil sample.

Figure 5:
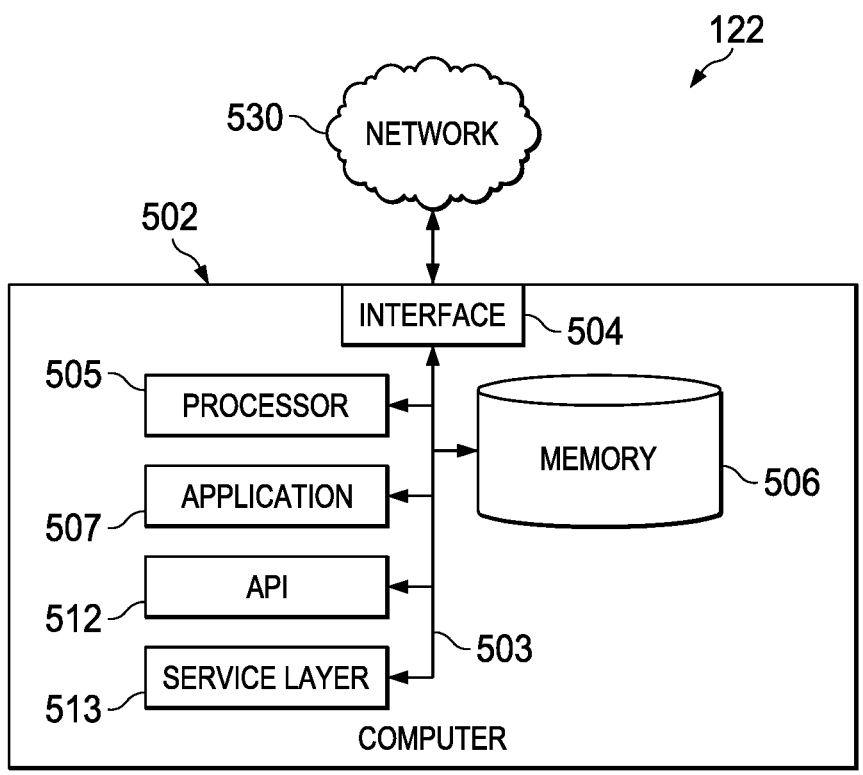
FIG. 5 is a high-level architectural block diagram of an example of a computer system for correlating and predicting LOAs in a lubrication oil sample obtained from a hydrocarbon well.

FIG. 5 is a block diagram 122 of an exemplary computer 502 used for predicting lubrication oil degradation based on LOA in a lubrication oil sample according to an implementation. The illustrated computer 502 is intended to encompass any computing device such as a server, desktop computer, laptop or notebook computer, wireless data port, smart phone, personal data assistant (PDA), tablet computing device, one or more processors within these devices, or any other suitable processing device, including both physical and virtual instances of the computing device. Additionally, the computer 502 may comprise a computer that includes an input device, such as a keypad, keyboard, touch screen, or other device that can accept user information, and an output device that conveys information associated with the operation of the computer 502, including digital data, visual and audio information, or a graphical user interface (GUI).

The computer 502 can serve as a client, network component, a server, a database or other persistency, or any other component of a computer system for predicting lubrication oil degradation based on LOA in a lubrication oil sample. The illustrated computer 502 is communicably coupled with a network 530. In some implementations, one or more components of the computer 502 may be configured to operate within a cloud-computing-based, local, global, or other environment.

At a high level, the computer 502 is an electronic computing device operable to receive, transmit, process, store, or manage data and information associated with predicting lubrication oil degradation based on LOA in a lubrication oil sample. According to some implementations, the computer 502 may also include or be communicably coupled with an application server, e-mail server, web server, caching server, streaming data server, business intelligence (BI) server, or other server.

The computer 502 can receive requests over network 530 from a client application (for example, executing on another computer 502) and respond to the received requests by processing the said requests in an appropriate software application. In addition, requests may also be sent to the computer 502 from internal users (for example, from a command console or by other appropriate access method), external or third parties, other automated applications, as well as any other appropriate entities, individuals, systems, or computers.

Each of the components of the computer 502 can communicate using a system bus 503. In some implementations, any or all the components of the computer 502, both hardware and software, may interface with each other or the interface 504 over the system bus 503 using an application programming interface (API) 512 or a service layer 513. The API 512 may include specifications for routines, data structures, and object classes. The API 512 may be either computer language-independent or -dependent and refer to a complete interface, a single function, or even a set of APIs. The service layer 513 provides software services to the computer 502 and other components (whether or not illustrated) that are communicably coupled to the computer 502. The functionality of the computer 502 may be accessible for all service consumers using this service layer. Software services, such as those provided by the service layer 513, provide reusable, defined business functionalities through a defined interface. For example, the interface may be software written in any suitable language providing data in extensible markup language (XML) format or other suitable format. While illustrated as an integrated component of the computer 502, alternative implementations may illustrate the API 512 and the service layer 513 as stand-alone components in relation to other components of the computer 502 and other components (whether or not illustrated) that are communicably coupled to the computer 502. Moreover, any or all parts of the API 512 and the service layer 513 may be implemented as child or sub-modules of another software module, enterprise application, or hardware module without departing from the scope of this disclosure.

The computer 502 includes an interface 504. Although illustrated as a single interface 504 in FIG. 5, two or more interfaces 504 may be used according to particular needs, desires, or particular implementations of the computer 502 and functionality for predicting lubrication oil degradation based on LOA. The interface 504 is used by the computer 502 for communicating with other systems in a distributed environment that are connected to the network 530. Generally, the interface 504 comprises logic encoded in software and hardware in a suitable combination and operable to communicate with the network 530. More specifically, the interface 504 may comprise software supporting one or more communication protocols associated with communications such that the network 530 or interface's hardware is operable to communicate signals within and outside of the illustrated computer 502.

The computer 502 includes a processor 505. Although illustrated as a single processor 505 in FIG. 5, two or more processors may be used according to particular needs, desires, or particular implementations of the computer 502. Generally, the processor 505 executes instructions and manipulates data to perform the operations of the computer 502. Specifically, the processor 505 executes the functionality for predicting lubrication oil degradation based on LOA in a lubrication oil sample.

The computer 502 also includes a memory 506 that holds data for the computer 502 and other components that can be connected to the network 530. For example, memory 506 can be a database storing LOA lubrication oil analysis data, and data consistent with this disclosure. Although illustrated as a single memory 506 in FIG. 5, two or more memories may be used according to particular needs, desires, or particular implementations of the computer 502 and functionality to predict lubrication oil degradation based on LOA in a lubrication oil sample. While memory 506 is illustrated as an integral component of the computer 502, in alternative implementations, memory 506 can be external to the computer 502.

The application 507 is an algorithmic software engine providing functionality according to particular needs, desires, or particular implementations of the computer 502, particularly with respect to functionality required for predicting lubrication oil degradation based on LOA in a lubrication oil sample. For example, application 507 can serve as one or more components, modules, and applications described with respect to any of the figures. Further, although illustrated as a single application 507, the application 507 may be implemented as multiple applications 507 on the computer 502. In addition, although illustrated as integral to the computer 502, in alternative implementations, the application 507 can be external to the computer 502.

There may be any number of computers 502 associated with, or external to, a computer system containing computer 502, each computer 502 communicating over network 530. Further, the terms "client," "user," and other appropriate terminology may be used interchangeably as appropriate without departing from the scope of this disclosure. Moreover, this disclosure contemplates that many users may use one computer 502, or that one user may use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, such as, one or more modules of computer program instructions encoded on a tangible, non-transitory computer-storage medium for execution by, or to control the operation of, data processing apparatus. Alternatively or in addition, the program instructions can be encoded on an artificially generated propagated signal, such as, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus and special purpose logic circuitry may be hardware-based and software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD-R, DVD-RAM, and DVD-ROM disks. The memory may store various objects or data, including caches, classes, frameworks, applications, backup data, jobs, web pages, web page templates, database tables, repositories storing business and dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), worldwide interoperability for microwave access (WI-MAX), a wireless local area network (WLAN) using, for example, 802.11 a/b/g/n and 802.20, all or a portion of the Internet, and any other communication system or systems at one or more locations. The network may communicate with, for example, internet protocol (IP) packets, frame relay frames, asynchronous transfer mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and software, may interface with each other or the interface using an application programming interface (API) or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in any suitable language providing data in any suitable format. The API and service layer may be an integral or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing may be advantageous and performed as deemed appropriate.

Moreover, the separation or integration of various system modules and components in the implementations described earlier should not be understood as requiring such separation or integration in all implementations, and it should be understood that the described program components and systems can generally be integrated together in a single software product or packaged into multiple software products.

Accordingly, the earlier provided description of example implementations does not define or constrain this disclosure. Other changes, substitutions, and alterations are also possible without departing from the spirit and scope of this disclosure.

What is claimed is:

1. A system to diagnose lubrication oil deterioration, the system comprising:
   a memory;
   a hardware processor interoperably coupled with the memory and configured to:
      guide a first light beam to a fresh lubrication oil sample obtained from a hydrocarbon well equipment;
      guide a second light beam to a deteriorated lubrication oil sample obtained from the hydrocarbon well equipment;
      detect a first light-induced fluorescence signal from the fresh lubrication oil sample;

detect a second light-induced fluorescence signal from the deteriorated lubrication oil sample;

process the first light-induced fluorescence signal and the second light-induced fluorescence signal to determine a respective damping effect or natural frequency of each of the first light-induced fluorescence signal and the second light-induced fluorescence signal;

based on results of processing the first light-induced fluorescence signal and the second light-induced fluorescence signal, determine a lubrication oil parameter for the fresh lubrication oil sample and a lubrication oil parameter for the deteriorated lubrication oil sample; and determine an amount of lubrication oil deterioration of the lubrication oil sample by correlating the lubrication oil parameter for the fresh lubrication oil sample and the deteriorated lubrication oil sample to a calibration curve.

2. The system of claim 1, wherein the hardware processor is configured to:

determine a temporal variation of a first fluorescence intensity from the first light-induced fluorescence signal; and determine a temporal variation of a second fluorescence intensity from the second light-induced fluorescence signal.

3. The system of claim 2, wherein the hardware processor is configured to:

determine a steady-state of the first light-induced fluorescence signal from the temporal variation of the first fluorescence intensity; and determine a steady-state of the second light-induced fluorescence signal from the temporal variation of the second fluorescence intensity.

4. The system of claim 3, wherein the hardware processor is configured to:

determine the lubrication oil parameter for the fresh lubrication oil sample from the steady-state of the first light-induced fluorescence signal; and determine the lubrication oil parameter for the deteriorated lubrication oil sample from the steady-state of the second light-induced fluorescence signal.

5. The system of claim 2, wherein the hardware processor is configured to represent each of the first fluorescence intensity and the second fluorescence intensity as a second order dynamic system corresponding to one of an over-damped oscillator with a damping ratio larger than 1 or an under-damped oscillator with a damping ratio smaller than 1.

6. The system of claim 1, wherein the hardware processor is configured to:

guide the first light beam at an acute angle on a front surface of a container holding the fresh lubrication oil sample; and guide the second light beam at an acute angle on a front surface of a container holding the deteriorated lubrication oil sample.

7. The system of claim 1, wherein the hardware processor is configured to:

filter each of the first light-induced fluorescence signal and the second light-induced fluorescence signal.

8. The system of claim 1, wherein the hardware processor is configured to capture each of the first light-induced fluorescence signal and the second light-induced fluorescence signal by a fast photodiode.

* * * * *